(12) United States Patent
Rodgers et al.

(10) Patent No.: US 8,936,713 B2
(45) Date of Patent: Jan. 20, 2015

(54) FILL SUFFICIENCY METHOD AND SYSTEM

(75) Inventors: James Iain Rodgers, Lochardil (GB);
Leanne Mills, Milton of Leys (GB);
Marco Cardosi, Croy (GB); Chris Leach, Inverness (GB); James Moffat, Inverness (GB)

(73) Assignee: Lifescan Scotland Limited, Inverness (GB)

( * ) Notice: Subject to any disclaimer, the term of this patent is extended or adjusted under 35 U.S.C. 154(b) by 1067 days.

(21) Appl. No.: 12/965,680

(22) Filed: Dec. 10, 2010

(65) Prior Publication Data

US 2011/0144915 A1 Jun. 16, 2011

Related U.S. Application Data

(60) Provisional application No. 61/285,916, filed on Dec. 11, 2009.

(51) Int. Cl.
G01N 27/327 (2006.01)

(52) U.S. Cl.
CPC ................................. G01N 27/3274 (2013.01)
USPC ..................... 205/777.5; 205/792; 204/403.14

(58) Field of Classification Search
USPC .............. 205/777.5, 792; 204/403.01–403.15
See application file for complete search history.

(56) References Cited

U.S. PATENT DOCUMENTS

| | | | |
|---|---|---|---|
| 5,582,697 A | 12/1996 | Ikeda et al. |
| 6,540,891 B1 | 4/2003 | Stewart et al. |
| 6,670,115 B1 | 12/2003 | Zhang et al. |
| 6,733,655 B1 | 5/2004 | Davis et al. |
| 7,083,712 B2 | 8/2006 | Morita et al. |
| 7,378,007 B2 | 5/2008 | Moerman et al. |
| 7,429,865 B2 | 9/2008 | Dreibholz et al. |
| 7,547,382 B2 | 6/2009 | Harding et al. |
| 2003/0098233 A1 | 5/2003 | Kermani et al. |
| 2003/0106809 A1 | 6/2003 | Kermani et al. |

(Continued)

FOREIGN PATENT DOCUMENTS

CA 2387599 A1 12/2002
CN 1424577 A 6/2003

(Continued)

OTHER PUBLICATIONS

Parkes, Joan L. et al., *A New Consensus Error Grid to Evaluate the Clinical Significance of Inaccuracies in the Measurement of Blood Glucose*, Diabetes Care, vol. 23 No. 8, 1143-1147 [2000].

(Continued)

*Primary Examiner* — J. Christopher Ball (57) ABSTRACT

Described and illustrated herein are one exemplary method and a measurement system having a meter and a test strip. The test strip has a first working electrode, reference electrode and second working electrode. In this method, acceptable fill data from known first current and known second current are used to predict an estimated second current at proximate the second time period (for a given batch of test strips) during the test sequence. The estimated second current at proximate the second time interval is then compared with a measured actual second current at proximate the second time interval during an actual test to determine if the measured actual second current is substantially equal to or within an acceptable percent deviation from the estimated second current so as to determine sufficient volume of a physiological fluid sample in the test strip.

5 Claims, 11 Drawing Sheets

(56) References Cited

U.S. PATENT DOCUMENTS

| | | |
|---|---|---|
| 2003/0109798 A1 | 6/2003 | Kermani |
| 2004/0138543 A1* | 7/2004 | Russell et al. ............ 600/345 |
| 2004/0154932 A1 | 8/2004 | Deng et al. |
| 2005/0139469 A1 | 6/2005 | Davies et al. |
| 2007/0045127 A1 | 3/2007 | Huang et al. |
| 2008/0011059 A1 | 1/2008 | Davis et al. |
| 2008/0093227 A1 | 4/2008 | Diamond et al. |
| 2009/0095071 A1 | 4/2009 | Wu et al. |
| 2009/0184004 A1 | 7/2009 | Chatelier et al. |
| 2009/0301899 A1 | 12/2009 | Hodges et al. |

FOREIGN PATENT DOCUMENTS

| | | |
|---|---|---|
| CN | 1558224 A | 12/2004 |
| CN | 1607387 A | 4/2005 |
| CN | 101432620 A | 5/2009 |
| EP | 1074832 A1 | 2/2001 |
| JP | 2002526759 A | 8/2002 |
| JP | 2007514931 A | 6/2007 |
| JP | 2007523327 A | 8/2007 |
| WO | 0020626 A1 | 4/2000 |
| WO | WO 2005/045417 A1 * | 5/2005 |
| WO | WO 2008/040998 A2 | 4/2008 |

OTHER PUBLICATIONS

European Patent Application No. 10252088.9, Extended European Search Report dated May 7, 2013, European Patent Office, 7 pages.
Patent Examination Report issued in related Australian Application No. 2010249255, Oct. 11, 2013, 3 pages.
Search Report issued in related Chinese Patent Application No. 201010602519.9, Jan. 17, 2014, 3 pages.
First Office Action issued in related Chinese Patent Application No. 201010602519.9, Jan. 28, 2014, 14 pages.
Notice of Reasons for Rejection issued in related Japanese Patent Application No. 2010-275896, Mar. 11, 2014, 2 pages.

* cited by examiner

FILL SUFFICIENCY METHOD AND SYSTEM

This application claims the benefits of priority under 35 USC §119 and/or §120 from prior filed U.S. Provisional Application Ser. No. 61/285,916 filed on Dec. 11, 2009, which application is incorporated by reference in its entirety into this application.

BACKGROUND

Electrochemical sensors have long been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

Electrochemical biosensors may be adversely affected by the presence of interfering substances in the test sample that may undesirably affect the measurement and lead to inaccuracies in the detected signal. Another source of inaccuracy is from insufficient sample being applied to the test strip. These sources of inaccuracy may cause an inaccurate glucose reading, leaving the patient unaware of a potentially dangerous blood sugar level.

It is known, for example, in U.S. Pat. No. 5,582,697, to have an additional fill detection electrode located downstream from the working electrode to determine that a sufficient volume of fluid has been applied to the test strip. An additional electrode increases the size of the electrode cell which increases the size of the sample required to fill the cell.

SUMMARY OF THE DISCLOSURE

Applicants have recognized a need for a system and method that can be used to determine volume sufficiency of a fluid sample applied to a test strip in which a separate fill detection electrode in not required.

In view of the foregoing and in accordance with one aspect, there is provided a method of operating a system having a meter and a test strip. The test strip includes a first working electrode, a shared reference electrode and a second working electrode in which all the electrodes are coated with a mediator layer. In one embodiment, a first reagent layer for measuring a first analyte concentration is disposed on a portion of the mediator layer covering the first working electrode and a second reagent layer for measuring a second analyte concentration is disposed on a portion of the mediator layer covering the second working electrode. In another embodiment, the first working electrode is coated only with a mediator layer.

The meter includes an electronic circuit for applying a first test voltage between the shared reference electrode and the first working electrode and for applying a second test voltage between the shared reference electrode and the second working electrode. The meter also includes a signal processor for measuring a first test current and a second test current and for calculating at least two analyte concentrations from the first and second test currents. The method may be achieved by applying a first voltage between the first working electrode, the shared reference electrode and the second working electrode in a test strip, measuring a current during the first time period at the first working electrode, applying a voltage other than first voltage for a second time period after the first time period between the shared reference electrode and the second working electrode, measuring a current during the second time period at the second working electrode with the meter, predicting an estimated second current during the second time period at the second working electrode based on the first current, evaluating a difference between the measured second current during the second time period and the estimated second current during the second time period at the second electrode and displaying an error condition indicating volume insufficiency if the difference between the measured second current during the second time period and the estimated second current during the second time period is greater than an acceptance limit.

In an embodiment, the first voltage is zero and is applied between the first working electrode, the shared reference electrode and the second working electrode for about zero seconds to about 4 seconds.

In an embodiment, the voltage other than first voltage for a second time period after the first time period includes from about 200 millivolts to about 500 millivolts.

In an embodiment, the estimated second current during the second time period is determined from the measured first current as correlated to known first current data and known second current data from sufficiently filled samples.

In an embodiment, the acceptance limit includes from about −40% to about +40%.

These and other embodiments, features and advantages will become apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1:
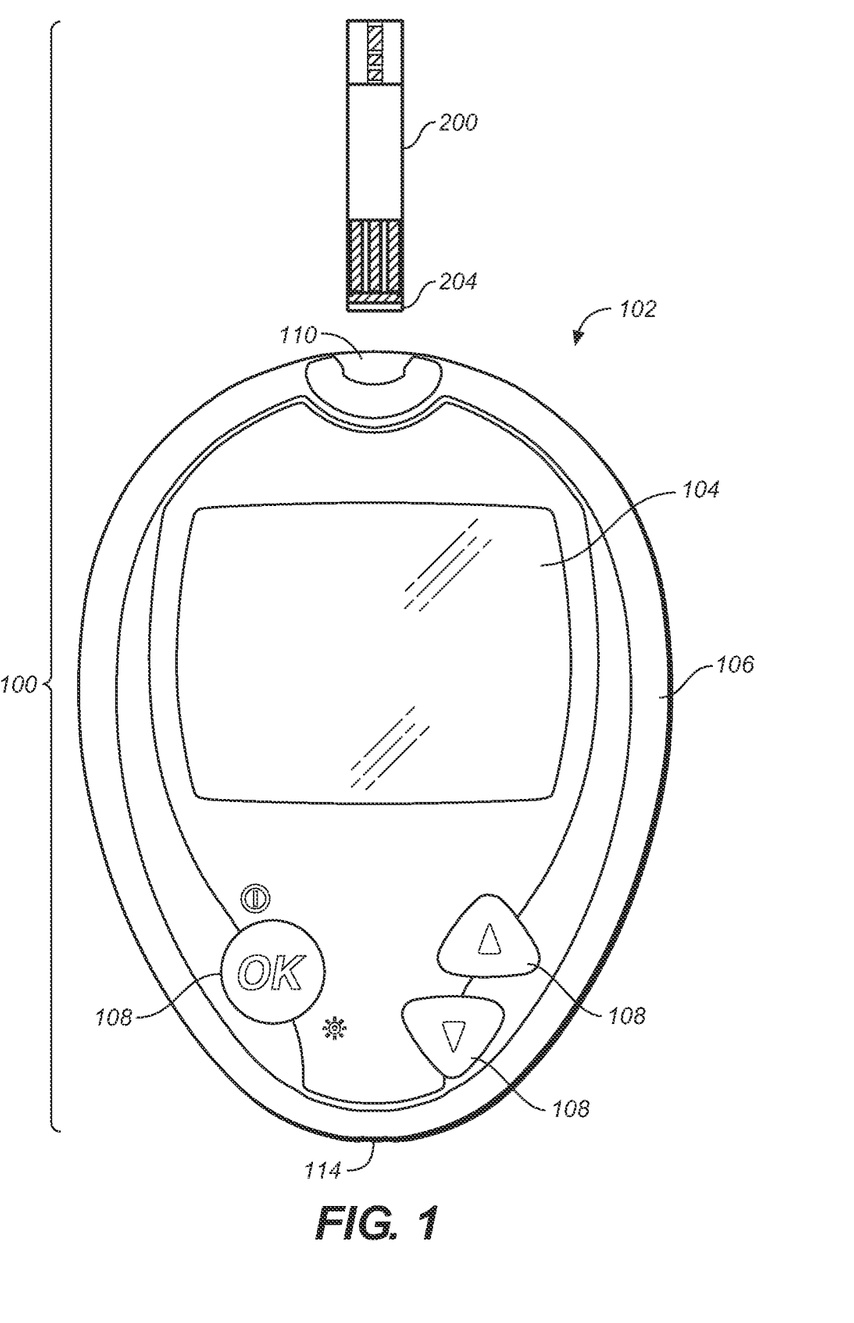
FIG. 1 illustrates an exemplary embodiment of a top view of a system for measuring at least two analyte concentrations.

FIG. 1 illustrates a system 100 for measuring at least two analyte concentrations in which system 100 includes a meter 102 and a test strip 200. Meter 102 includes a display 104, a housing 106, a plurality of user interface buttons 108, and a strip port 110. Meter 102 further includes electronic circuitry within housing 106 such as a memory 120, a microprocessor 122, electronic components for applying a test voltage, and also for measuring at least two test current values. A proximal portion 204 of test strip 200 may be inserted into strip port 110. Display 104 may output at least two analyte concentrations, e.g., glucose and/or ketone concentration, and may be used to show a user interface for prompting a user on how to perform a test. The plurality of user interface buttons 108 allow a user to operate meter 102 by navigating through the user interface software. Display 104 may optionally include a backlight.

An optional data port 114 accepts a suitable connector attached to a connecting lead, thereby allowing meter 102 to be linked to an external device such as a personal computer. Data port 114 may be any port that allows for transmission of data (serial or parallel) such as, for example, serial or parallel port in wired or wireless form. A personal computer, running appropriate software, allows entry and modification of set-up information (e.g. the current time, date, and language), and may perform analysis of data collected by meter 102. In addition, the personal computer may be able to perform advanced analysis functions, and/or transmit data to other computers (i.e. over the internet) for improved diagnosis and treatment. Connecting meter 102 with a local or remote computer facilitates improved treatment by health care providers.

Figure 2:
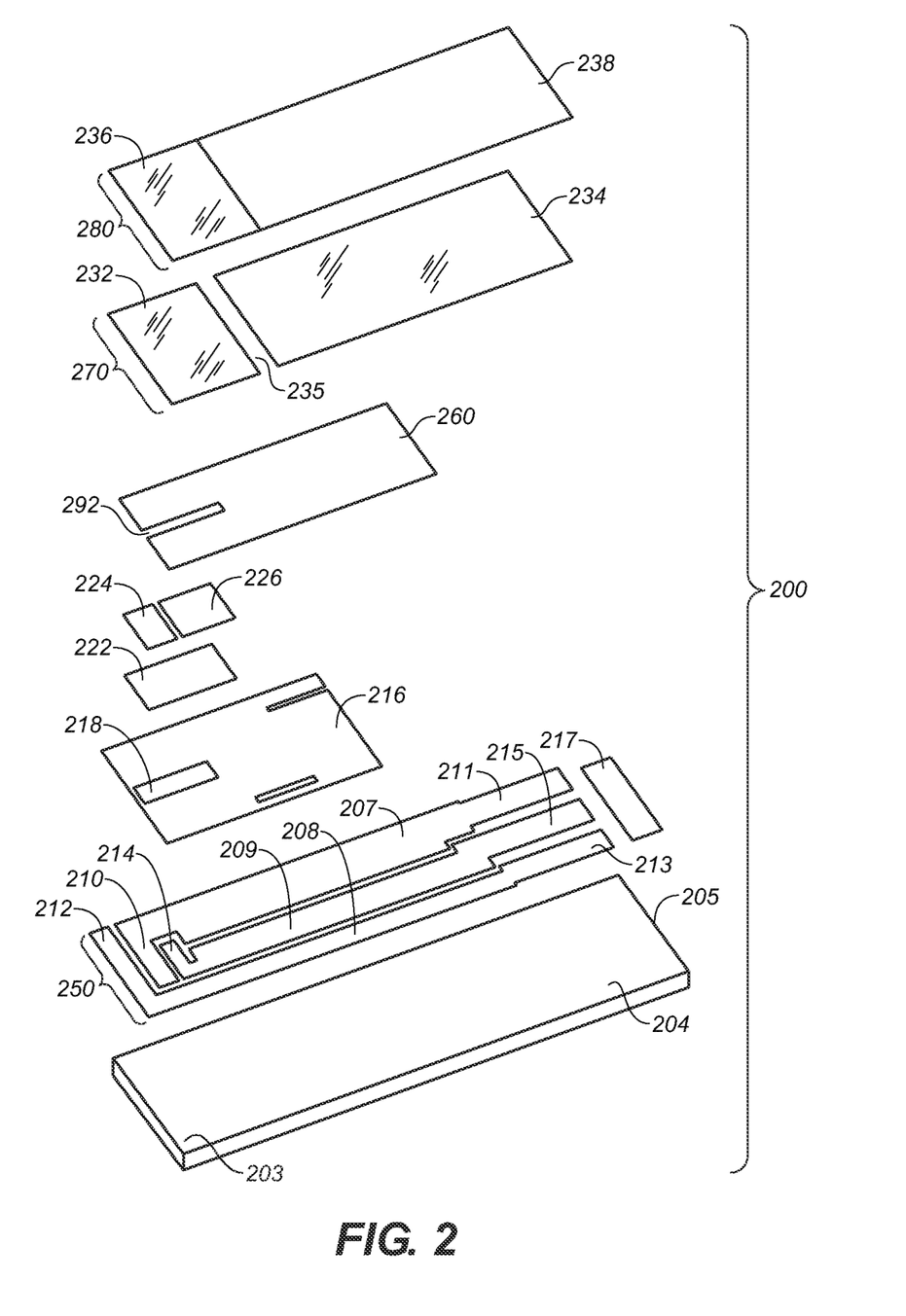
FIG. 2 illustrates an exemplary embodiment of a perspective exploded view of a test strip.
Figure 3:
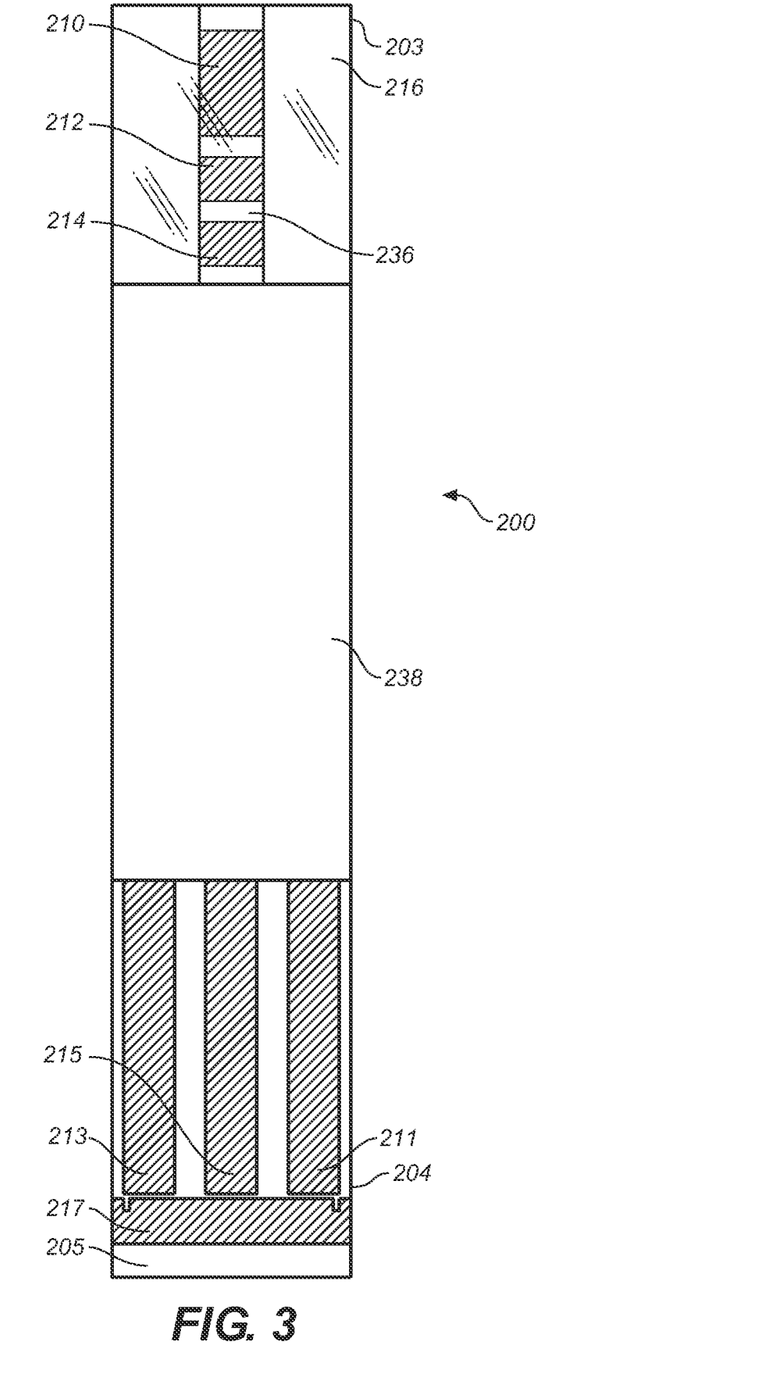
FIG. 3 illustrates an exemplary embodiment of a top view of the test strip shown in FIG. 2.

FIGS. 2 and 3 are exemplary exploded perspective and top assembled views, respectively, of test strip 200, which may include seven layers disposed on a substrate 205. The seven layers disposed on substrate 205 may be a conductive layer 250, an insulation layer 216, a mediator layer 222, a first reagent layer 224 and a second reagent layer 226, an adhesive layer 260, a hydrophilic layer 270, and a top layer 280. Test strip 200 may be manufactured in a series of steps where the conductive layer 250, insulation layer 216, mediator layer 222, first reagent layer 224, second reagent layer 226 and adhesive layer 260 are sequentially deposited on substrate 205 using, for example, a screen-printing process. Hydrophilic layer 270 and top layer 280 may be disposed from a roll stock and laminated onto substrate 205 as either an integrated laminate or as separate layers. Test strip 200 has a distal portion 203 and a proximal portion 204, as shown in FIG. 2.

Test strip 200 may include a sample-receiving chamber 292 through which a blood sample may be drawn. Sample-receiving chamber 292 may include an inlet at a proximal end of test strip 200. An outlet or air vent is included in hydrophilic layer 270, as will be described below. A blood sample may be applied to the inlet to fill a sample-receiving chamber 292 so that at least two analyte concentrations may be measured. The side edges of a cut-out portion of adhesive layer 260 located adjacent to first and second reagent layers 224 and 226 define a wall of sample-receiving chamber 292, as illustrated in FIG. 2. A bottom portion or "floor" of sample-receiving chamber 292 may include a portion of substrate 205, conductive layer 250, and insulation layer 216. A top portion or "roof" of sample-receiving chamber 292 may include distal hydrophilic portion 232.

For test strip 200, as illustrated in FIG. 2, substrate 205 may be used as a foundation for helping support subsequently applied layers. Substrate 205 may be in the form of a polyester sheet such as a polyethylene tetraphthalate (PET) material commercially available by suppliers such as, for example, Mitsubishi. Substrate 205 may be in a roll format, nominally 350 microns thick by 370 millimeters wide and approximately 60 meters in length.

A conductive layer is required for forming electrodes that may be used for the electrochemical measurement of glucose. Conductive layer 250 may be made from a carbon ink that is screen-printed onto substrate 205. In a screen-printing process, carbon ink is loaded onto a screen and then transferred through the screen using a squeegee. The printed carbon ink may be dried using hot air at about 140° C. The carbon ink may include VAGH resin, carbon black, graphite (KS15), and one or more solvents for the resin, carbon and graphite mixture. More particularly, the carbon ink may incorporate a suitable ratio of carbon black: VAGH resin in the carbon ink, which is commercially available from, for example, DuPont, Fujifilm Sericol, Gwent, Acheson, or Eltecks.

For test strip 200, as illustrated in FIG. 2, conductive layer 250 may include a first working electrode 212, a second working electrode 214, a reference electrode 210 that is shared by the first and second working electrodes 212 and 214, a reference contact pad 211, a first contact pad 213, a second contact pad 215, a reference electrode track 207, a first working electrode track 208, a second working electrode track 209, and a strip detection bar 217. In the embodiment shown in FIG. 2, reference electrode 210 is located in between first working electrode 212 and second electrode 214 such that cross-talk between first and second working electrodes 212 and 214 is minimized. Also, first working electrode 212 is upstream of reference electrode 210 and second working electrode 214. In another embodiment (not shown), second working electrode 214 is upstream of reference electrode 210 and first working electrode 212.

The conductive layer may be formed from a carbon ink Reference contact pad 211, first contact pad 213 and second contact pad 215 may be configured to electrically connect to a test meter. Reference electrode track 207 provides an electrically continuous pathway from reference electrode 210 to reference contact pad 211. Similarly, first working electrode track 208 provides an electrically continuous pathway from first working electrode 12 to first contact pad 213. Similarly, second working electrode track 209 provides an electrically continuous pathway from second working electrode 214 to second contact pad 215. Strip detection bar 217 is electrically connected to reference contact pad 211. A test meter may detect that test strip 200 has been properly inserted by measuring a continuity between reference contact pad 211 and strip detection bar 217.

Insulation layer 216 may include a rectangular aperture 218 that exposes a portion of reference electrode 210, first working electrode 212, and second working electrode 214, which may be wetted by a liquid sample. The area of first working electrode 212, second working electrode 214, and reference electrode 210 may be defined as the area exposed to the liquid sample. In addition to defining an electrode area, insulation layer 216 prevents a liquid sample from touching the electrode tracks 207, 208, and 209. It is important to accurately define the functional area of a working electrode because the magnitude of the test current is directly proportional to the effective area of the electrode. As an example, insulation layer 216 may be Ercon ink that may be purchased from Ercon, Inc. The test strip at this point may be treated with plasma. The plasma, consisting of ionised, highly energetic particles, is created by high voltage AC at atmospheric temperatures and pressures. The resulting plasma, placed approximately 100 millimeters from the substrate, is swept downstream in an air current to impact the substrate. Plasma treatment is used to modify the surface of the screen printed carbon based electrodes. This surface modification is believed to increase the electrochemical activity of the carbon surface and increases the surface energy of the printed layers allowing for better adhesion between them and subsequently printed layers. Plasma treatment is also believed to improve the electrochemistry of the carbon surface making the reaction with the mediator more ideal.

Mediator layer 222 includes a mediator such as, for example, ferricyanide and a cofactor such as, for example, nicotinamide adenine dinucleotide (NADH). In one embodiment, mediator layer 222 may include potassium ferricyanide, NADH, Tris-HCL buffer, hydroxyethylcellulose, DC 1500 Antifoam, Cabosil TS 610, poly (vinyl pyrrolidone vinyl acetate), Triton X-100, calcium chloride and analar water.

First and second reagent layers 224 and 226 are each disposed on mediator layer 222, as illustrated in FIG. 2. Second reagent layer 226 is disposed on mediator layer 222 above second working electrode 214 and reference electrode 210. First and second reagent layers 224 and 226 each may include chemicals such as an enzyme which selectivity reacts with an analyte of interest such that the analyte concentration may be determined. Exemplary analytes of interest for monitoring diabetes include glucose and ketones. In one embodiment, first reagent layer 224 includes at least one enzyme that selectively reacts with ketones and second reagent layer 226 includes an enzyme that selectively reacts with glucose. In yet another embodiment (not shown), first reagent layer 224 does not include an enzyme that selectively reacts with an analyte and second reagent layer 226 includes an enzyme that selectively reacts with glucose.

In one embodiment, the components in the reagent layer used to determine the ketone concentration includes beta-hydroxybutyrate dehydrogenase (BHD), Tris-HCL buffer, hydroxyethylcellulose, potassium ferricyanide, DC 1500 Antifoam, Cabosil TS 610, poly(vinyl pyrrolidone vinyl acetate), Triton X-100, calcium chloride and analar water. In another embodiment, the reagent layer used to measure ketones includes a second enzyme such as, for example, diaphorase Examples of enzymes suitable for use in the reagent layer for measuring glucose may include either glucose oxidase or glucose dehydrogenase. More specifically, the glucose dehydrogenase may have a pyrrylo-quinoline quinone (PQQ) cofactor or a flavin adenine dinucleotide (FAD) cofactor. In one embodiment, the components in the reagent layer that is used to determine the glucose concentration may include glucose oxidase, Tris-HCL buffer, hydroxyethylcellulose, potassium ferricyanide, DC 1500 Antifoam, Cabosil TS 610, poly(vinyl pyrrolidone vinyl acetate), Triton X-100, calcium chloride and analar water.

First and second reagent layers 224 and 226 may be formed from a reagent ink, which is disposed onto mediator layer 222 and dried. Note that the reagent ink may also be referred to as an enzyme ink or reagent formulation. A reagent ink typically contains a liquid, such as a buffer, for dispersing and/or dissolving materials used for the electrochemical detection of an analyte such as glucose. In one embodiment, first and second reagent layers 224 and 226 may be screen-printed in two successive steps onto mediator layer 222. Reagent ink may be loaded onto a screen until it is flooded. Next, a squeegee may be used to transfer the reagent ink through the screen and onto mediator layer 222. After the deposition, the reagent ink may be dried using hot air at about 50° C.

In one embodiment, the area of first reagent layer 224 is sufficiently large to cover the entire area of first working electrode 212 and second reagent layer 226 is sufficiently large to cover the entire area of second working electrode 214 and reference electrode 210. Each of first and second reagent layers 224 and 226 include a width and a length that is sufficiently large to at least account for the largest electrode area that may be used in test strip 200. The width of first and second reagent layers 224 and 226 may be about 2 millimeters, which is more than double a width of rectangular aperture 218.

Referring to FIG. 2, an adhesive layer 260 may be disposed on test strip 200 after the deposition of first and second reagent layers 224 and 226. Portions of adhesive layer 260 may be aligned to be immediately adjacent to, touch, or partially overlap with first and second reagent layers 224 and 226. Adhesive layer 260 may include a water based acrylic copolymer pressure sensitive adhesive which is commercially available from suppliers. Adhesive layer 260 is disposed on a portion of insulation layer 216, conductive layer 250, and substrate 205. Adhesive layer 260 binds hydrophilic layer 270 to test strip 200.

Hydrophilic layer 270 may include a distal hydrophilic portion 232 and proximal hydrophilic portion 234, as illustrated in FIG. 2. A gap 235 is included between distal hydrophilic portion 232 and proximal hydrophilic portion 234. Gap 235 serves as a side vent for air as blood fills sample-receiving chamber 292. Hydrophilic layer 270 may be a polyester having one hydrophilic surface such as an anti-fog coating, which is commercially available.

The final layer to be added to test strip 200 is top layer 280, as illustrated in FIG. 2. Top layer 280 may include a clear portion 236 and opaque portion 238. Top layer 280 is disposed on and adhered to hydrophilic layer 270. Top layer 280 may be a polyester that has an adhesive coating on one side. It should be noted that the clear portion 236 substantially overlaps distal hydrophilic portion 232, which allows a user to visually confirm that the sample-receiving chamber 292 may be sufficiently filled. Opaque portion 238 helps the user observe a high degree of contrast between a colored fluid such as, for example, blood within the sample-receiving chamber 292 and the opaque portion 238.

Figure 5:
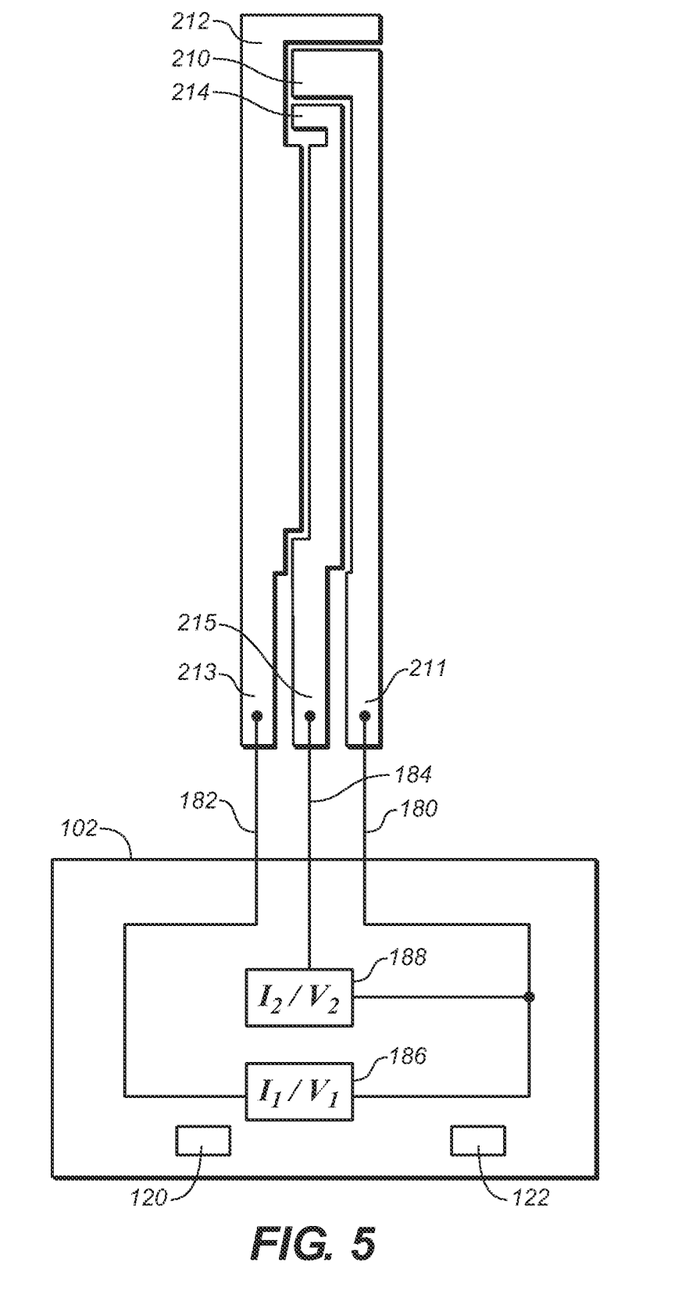
FIG. 5 illustrates an exemplary embodiment of a schematic of the functional components of the meter shown in FIG. 1 forming an electrical connection with the test strip of FIGS. 2 and 3.

FIG. 5 shows a simplified schematic of meter 102 interfacing with test strip 200. Meter 102 includes a reference connector 180, a first connector 182 and a second connector 184, which respectively form an electrical connection to reference contact 211, first contact 213 and second contact 215. The three aforementioned connectors are part of strip port 110. When performing a test, a first test voltage source 186 may apply a first test voltage $V_1$ between first working electrode 212 and reference electrode 210. As a result of first test voltage $V_1$, meter 102 may then measure a first test current $I_1$. In a similar manner, second test voltage source 188 applies a second test voltage $V_2$ between second working electrode 214 and reference electrode 210. As a result of second test voltage $V_2$, meter 102 may then measure a second test current $I_2$. In an embodiment, first test voltage $V_1$ and second test voltage $V_2$ may be about equal.

Figure 4A:
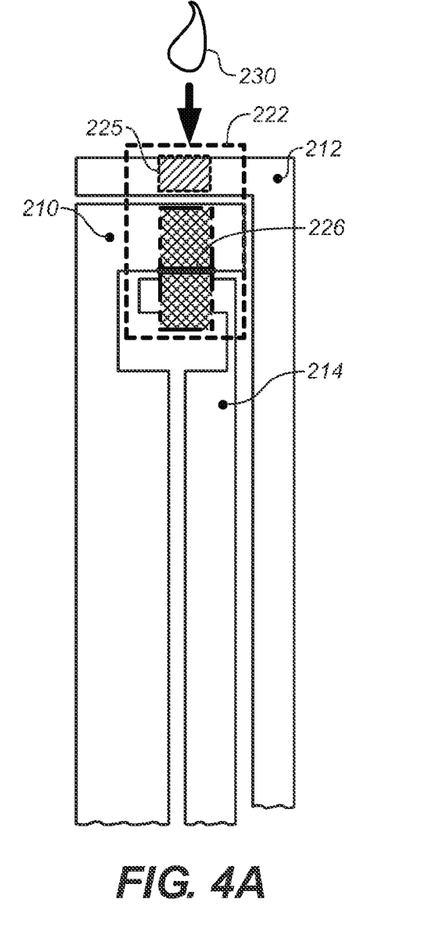
FIGS. 4A and 4B illustrate exemplary embodiments of a top view of a mediator layer and a reagent layer disposed on a conductive layer on a distal portion of a test strip.

As illustrated in FIG. 4A, all three electrodes (first working electrode 212, reference electrode 210, and second working electrode 214) are coated with a matrix layer having a suitable mediator, such as, for example, ruthenium or ferricyanide, disposed therein. A first enzyme reagent 225 is deposited over at least a portion of each of the first working electrode 212 and reference electrode 210. A second enzyme reagent 226 is deposited over the reference electrode 210 and second working electrode 214. This arrangement is believed to allow for detection of two different analytes.

Figure 4B:
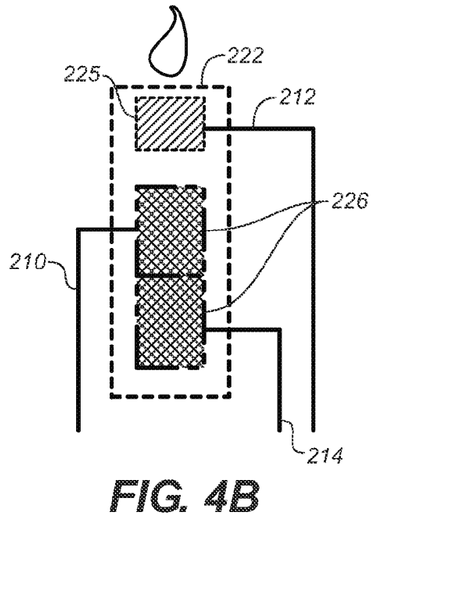

To explain the operation of this embodiment, reference is made to the schematic arrangement of a portion of the test strip in FIG. 4B. In FIG. 4B, all of the electrodes (210, 212, and 214) of the test strip are covered by the matrix layer 222 that has a suitable mediator (e.g., ferricyanide) dispersed therein. The test strip is inserted into the meter which applies a first voltage of about 0V to each electrode pair (first pair being first working electrode 212 and reference electrode 210 and the second pair being the second working electrode 214 and reference electrode 210). When the test strip is filled with blood 230 which contains a plurality of analytes (e.g., ketones and glucose). The enzymes react with ferricyanide once it is wetted with blood 230 to form ferrocyanide. With the first voltage (e.g., ~0V) being maintained, electro-catalytic reoxidation of ferrocyanide back to ferricyanide is believed not to occur until a second voltage (e.g., of about 400 mV) is applied. Where the second enzyme reagent 226 includes glucose dehydrogenase (which may include PQQ cofactor or FAD cofactor), the reaction at second working electrode 214 is faster, which allows ferrocyanide to build up rapidly at the second working electrode 214. Any ferrocyanide built up at first working electrode 212 is believed to be far less than at the second working electrode 214. Hence, a concentration gradient of ferrocyanide is established between first working electrode 212 and second working electrode 214, which is believed to generate a potential difference between first working electrode 212 and second working electrode 214.

However, since all three electrodes are electrically connected with the sample 230 acting as a salt bridge, a circuit is created, which generates a second negative current flow to restore the potential due to the applied first voltage (e.g., ~0V). This is believed to cause oxidation of ferrocyanide to ferricyanide at second working electrode 214 and a corresponding reduction of ferrocyanide to ferricyanide at first working electrode 212. Effectively, during the first time period with the first voltage (e.g., ~0V) applied, second working electrode 214 acts as a "working" electrode and the first working electrode 212 acts as a "reference" electrode with the assumption that any reverse current flowing in the first pair of electrodes (212 and 210) is proportionately small. Because the second enzyme reagent 226 is deposited to substantially cover both the second working electrode 214 and the reference electrode 210, the reference electrode 210 is believed to act during the first time period as a second working electrode with the first working electrode 212 acting as a lone reference electrode. Since the second current being measured during the second time period is a single electrode measurement whereas the current measured during the first time period is effectively derived from two aggregated electrodes (i.e., second working 214 and reference electrode 210), it is believed that if the first measured current during the first time period and the second measured current during the second time period show good correlation then it can be assumed that the reference electrode reaction during the first time period was similar to the second working electrode reaction during the first time period. This similarity therefore implies that the electrodes were sufficiently covered with blood sample 230, i.e., a sufficiently filled test strip in which both the second working electrode 214 and reference electrode 210 were sufficiently covered and therefore behaved similarly.

Conversely, if there was poor agreement between the second current measured during the second time period for the second working electrode 214 and the first current measurement during the first time period for the first electrode pair (first working electrode 212 and reference electrode 210), then it is believed that a likely source of this discrepancy would be an unequal response from the two normally equivalent electrodes during the first time period, implying that the electrodes were insufficiently filled.

Hence, by applying a suitable first voltage (e.g., about 0 volt) to first working electrode 212 and the reference electrode 210 for a first time period and a second voltage other than the first voltage for a second time period while measuring a second current generated by the second working electrode 214 and reference electrode 210 and comparing this measured second current with an estimated second current for a physiological sample 230 deposited onto three electrodes of the strip, applicants have been able to detect sufficient sample filling of the three electrodes without the need for a fourth electrode.

Figure 6:
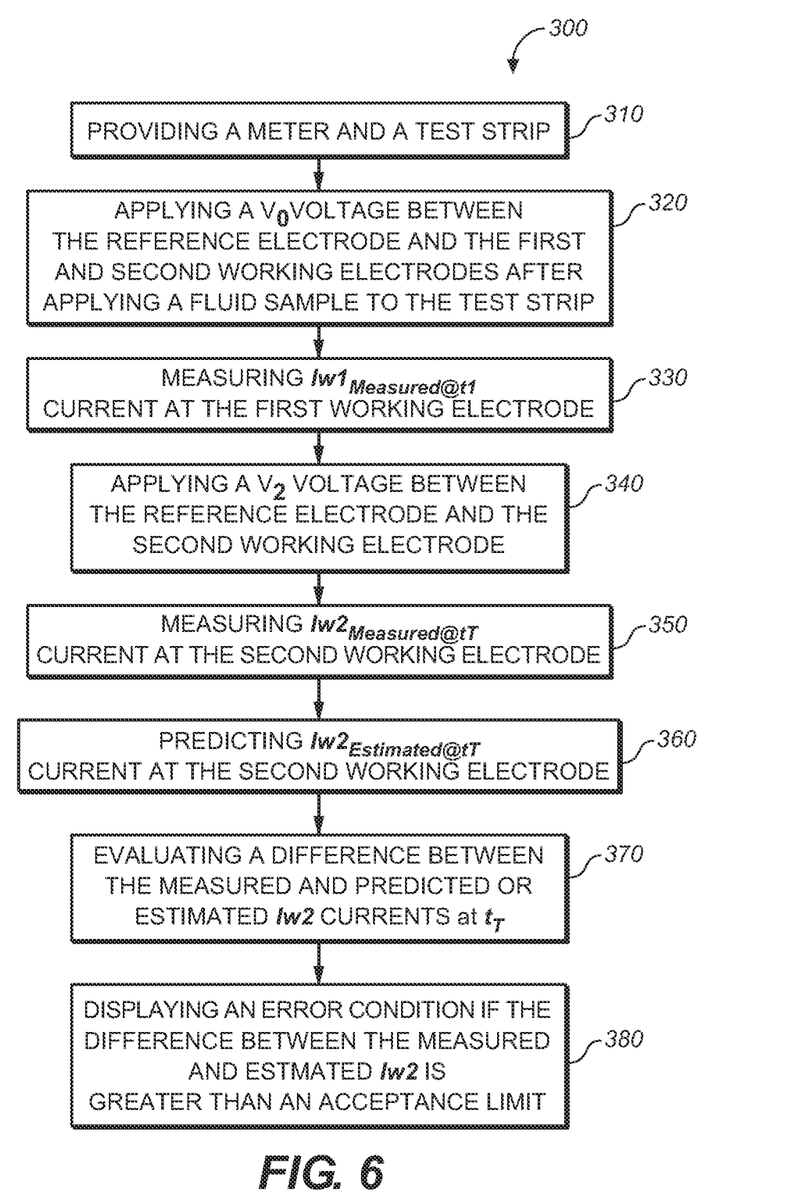
FIG. 6 illustrates an exemplary embodiment of a flow chart of a method of determining volume sufficiency using the system shown in FIG. 1.

Referring to FIG. 6, a method 300 for determining the volume sufficiency of a fluid sample applied to a test strip that uses the aforementioned meter 102 and test strip 200 embodiments will now be described. In exemplary step 310, a meter 102 and a test strip 200 are provided. Meter 102 includes electronic circuitry that can be used to apply (FIG. 7) at least one first test voltage $V_0$ during time period $t_1$ and at least one second test voltage $V_2$ after $t_1$ to $t_T$ to the test strip and to measure a first current $Iw1_{Measured@t1}$ (during the first time period $t_1$) flowing through first working electrode 212 and a second current $Iw2_{Measured@tT}$ (during the second time period $t_T$) flowing through second working electrode 214. In exemplary step 320, after a fluid sample is applied to test strip 200, first test voltage $V_0$, for example, about 0 millivolts is applied between first working electrode 212, second working electrode 214 and reference electrode 210 at $t_0$ for a first time period $t_1$. First time period $t_1$ is typically from about 0 seconds to about 4 seconds and is more typically about 3 seconds.

Figure 7:
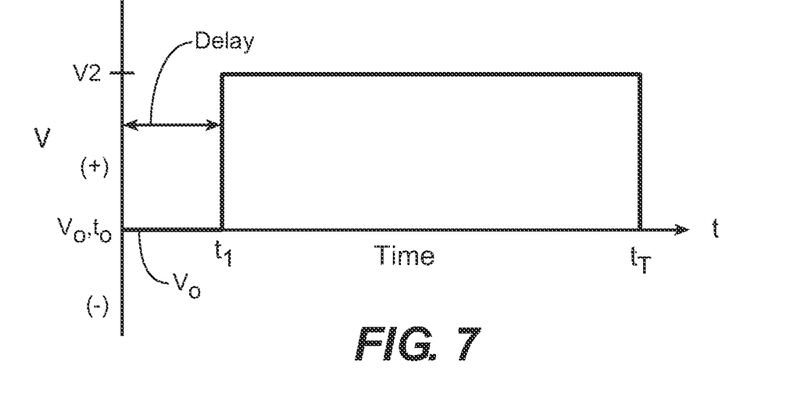
FIG. 7 illustrates an exemplary embodiment of a chart showing test voltages applied by the meter to the test strip.
Figure 8A:
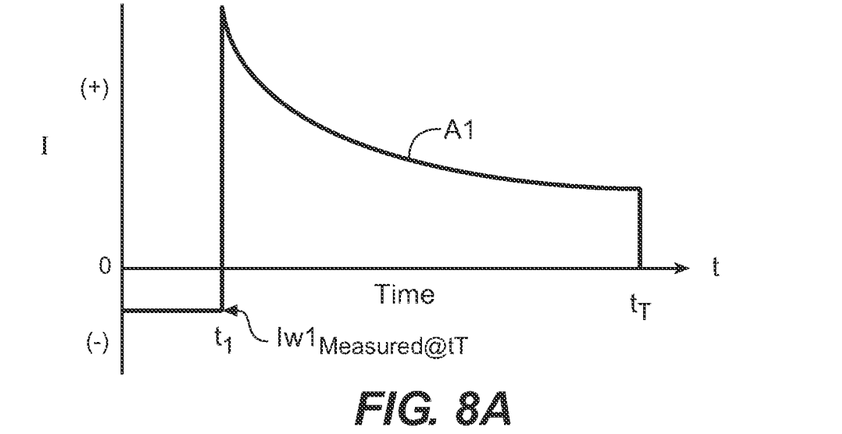
FIG. 8A illustrates an exemplary embodiment of a chart showing test currents generated when the test voltages of FIG. 7 are applied to the test strip.
Figure 8B:
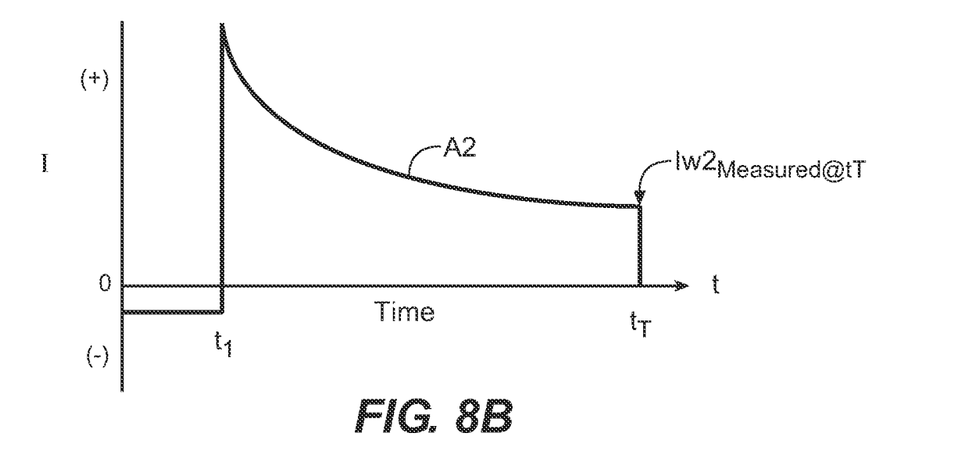
FIG. 8B illustrates the test current generated at the second electrode when test voltages of FIG. 7 are applied to the test strip.

FIG. 8A is an exemplary time to current chart of a current transient A1 (i.e., the measured electrical current response in nanoamperes as a function of time) that is measured when first test voltage $V_0$ and second test voltage $V_2$ of FIG. 7 are applied to the first working electrode of test strip 200. FIG. 8A also shows a current transient A2 for the second working electrode. In exemplary step 330, at or near the end of first time period $t_1$, first test current $Iw1_{Measured@t1}$ between first working electrode 212 and reference electrode 210 is measured (and normally recorded in the meter). In exemplary step 340, after first time period $t_1$, second test voltage $V_2$ is applied between second working electrode 214 and reference electrode 210 at time $t_1$ for a total test time $t_T$.

At time $t_T$ a second test current $Iw2_{Measured@tT}$ from the second working electrode 214 and reference electrode 210 is measured (and normally recorded in the meter) at or near the end of second test voltage $V_2$. Second test voltage $V_2$ is applied between second working electrode 214 and reference electrode 210 may be generally from about +100 millivolts to about +600 millivolts. In one embodiment in which second working electrode 212 is carbon ink and the mediator is ferricyanide, second test voltage $V_2$ is about +400 millivolts. Other mediator and electrode material combinations may require different test voltages. The duration of second test voltage $V_2$ may be generally from about 2 and 6 seconds and is typically about 5 seconds. Typically, time $t_T$ is measured relative to time $t_1$. In practice, second test current $Iw2_{Measured@tT}$ is the average of a set of measurements obtained over a short interval, for example, five measurements obtained at 0.01 second intervals starting at $t_T$.

In exemplary step 360, known first test current $Iw1_{Known@t1}$ and known second current $Iw2_{Known-tT}$ are determined from a calibration data stored in meter 102. The calibration curve may be generated at the factory by graphing the known first test current $Iw1_{Known@t1}$ as a function of the known second test current $Iw2_{Known@tT}$ at $t_T$ from samples with known good fill data, such as for example, in FIG. 8C.

Figure 8C:
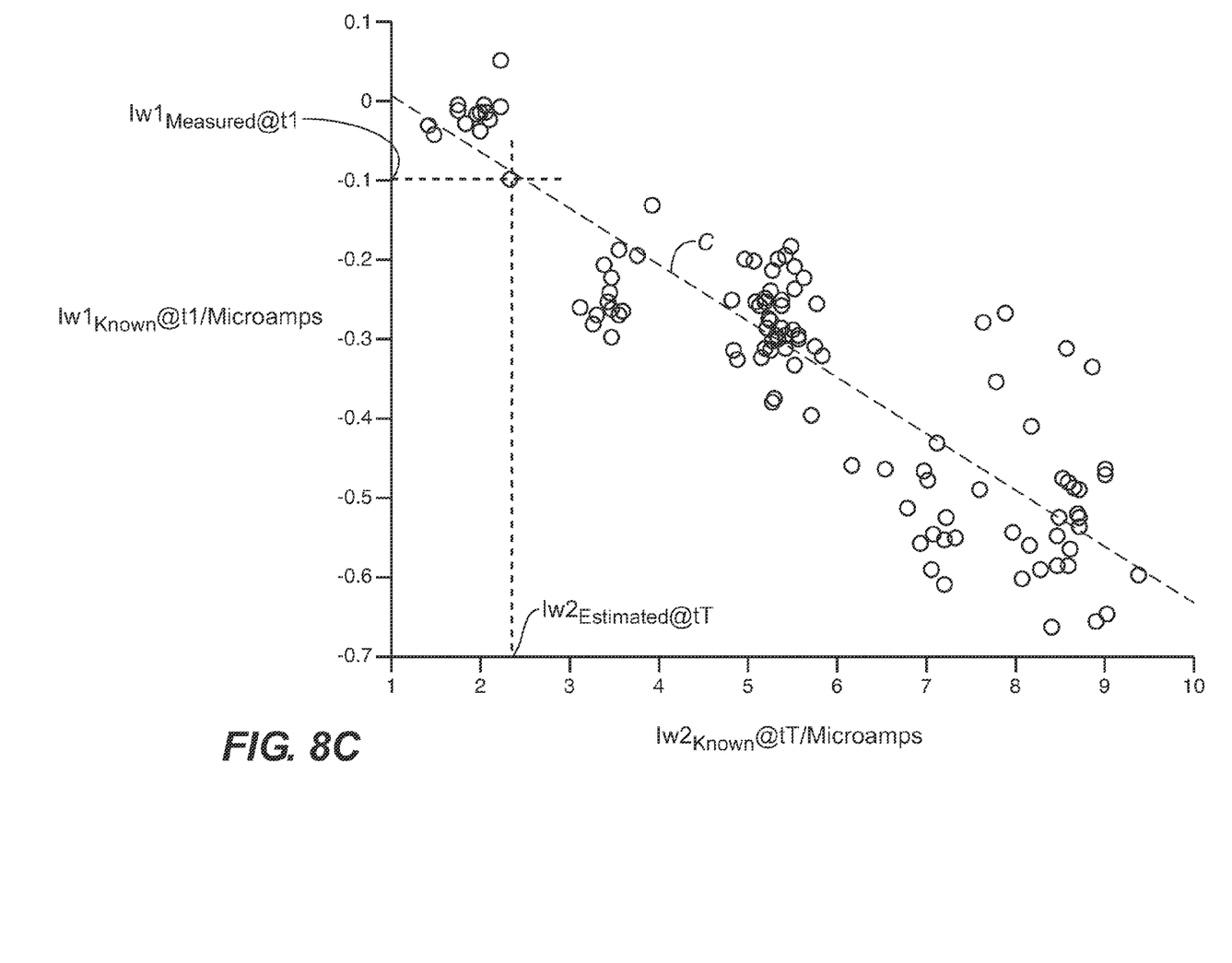
FIG. 8C illustrates the correlation between the current generated at the first electrode at $t_1$ and the current at the second electrode at $t_T$ based on historical data generated for a group of calibrated test strips.

FIG. 8C shows that for each first current $Iw1_{Known@t1}$ at the end of the first time period $t_1$, there is a corresponding second current $Iw2_{Known@tT}$ at the end of the second time period $t_T$ clustered about various areas between these two current values for samples with sufficient fill volume. From these first current and second current, a correlation line C as shown in FIG. 8C, may be generated from known acceptable sample filling data.

Figure 8D:
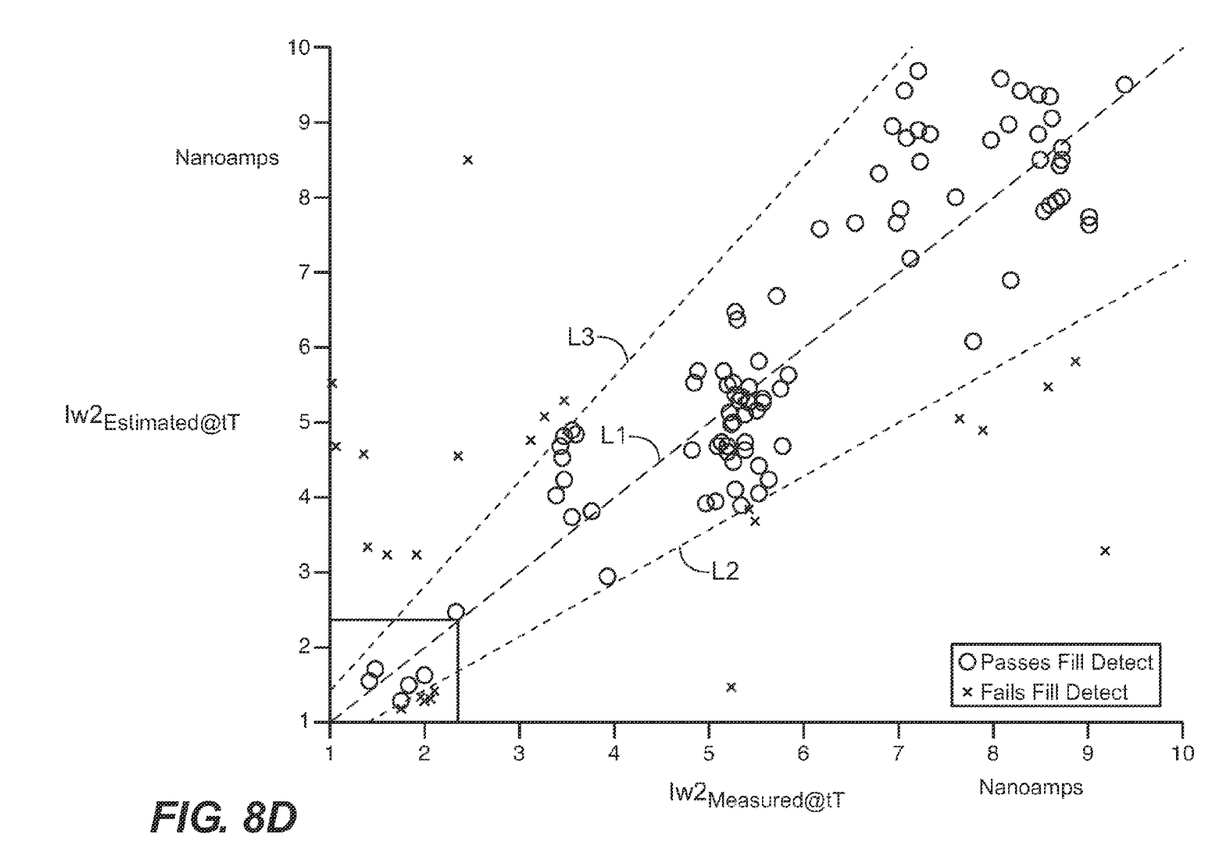
FIG. 8D illustrates the correlation between the second current at $t_T$ and the actual second current at $t_T$.

From the correlation between measured first current and known second current in FIG. 8C, an estimated current $Iw2_{Estimated@tT}$ can be determined by locating where the measured first current $Iw1_{Measured@t1}$ (from step 330) would be along line C of FIG. 8C and plotting where such value of the measured first current $Iw1_{Measured@t1}$ would correspond to an estimated second current along the x-axis of FIG. 8C. It is noted that this process could also be achieved via a look up table. This estimated current, designated as $Iw2_{Estimated@tT}$ is compared with the measured second current $Iw2_{Measured@tT}$ at second time period $t_T$ to determine if there are unacceptable deviations from a one-to-one correspondence. From FIG. 8D, it can be seen that a sufficient correlation between estimated second current and measured second current can be established (L1) with suitable standard of deviations that are indicative of acceptable fill (L2 and L3).

In short, the measured first current at $t_1$ is used in conjunction with known good fill data (FIG. 8C) to predict an estimated second current at the second time period $t_T$ (for a given batch of test strips). The estimated second current at time $t_T$ (as derived from FIG. 8C) is then compared with measured actual second current at $t_T$ in FIG. 8D to determine if the measured actual second current is substantially equal to or within an acceptable percent deviation from the estimated second current.

In exemplary step 380, an error condition is displayed if the difference between the measured $Iw2_{Measured@tT}$ and estimated second current $Iw2_{Estimated@tT}$ is greater than an acceptance limit. In an embodiment, the measured second current during the second time period may differ from the estimated second current during the second time period by no more than about +/−40 percent.

Example 1

Determination of Volume Sufficiency with a Test Strip as Shown in FIGS. 2 and 3

Test strips as shown in FIGS. 2 and 3 were tested with 154 whole blood samples having glucose concentrations ranging from about 60 mg/dL to about 500 mg/dL and hematocrit levels ranging from about 30 to about 55%. For each of these samples, the a current during the first time period was measured at the first working electrode at approximately 3 seconds after applying a first voltage of approximately 0 millivolts to the test strip. The current during the second time period was also measured at the second working electrode at approximately 5 seconds after applying a second voltage (of a value other than the first voltage) for a second time period after the first time period of 400 millivolts to the test strip. For 30 out of a total of 154 samples, insufficient sample was applied to the test strip.

Figure 9A:
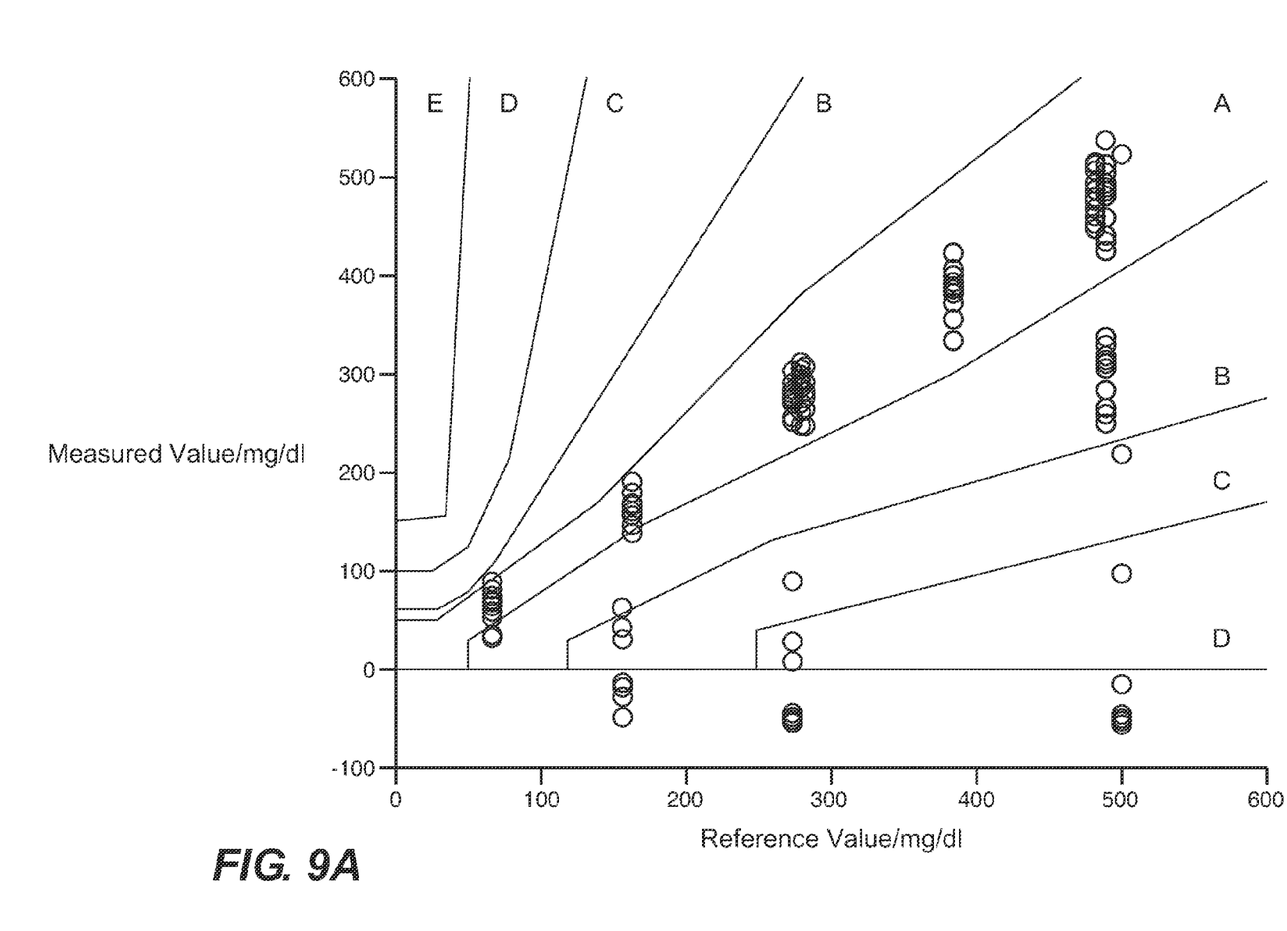
FIG. 9A illustrates a Concensus Error Grid before applying an exemplary embodiment of the subject method to the data obtained with test strips as shown in FIGS. 2 and 3.
Figure 9B:
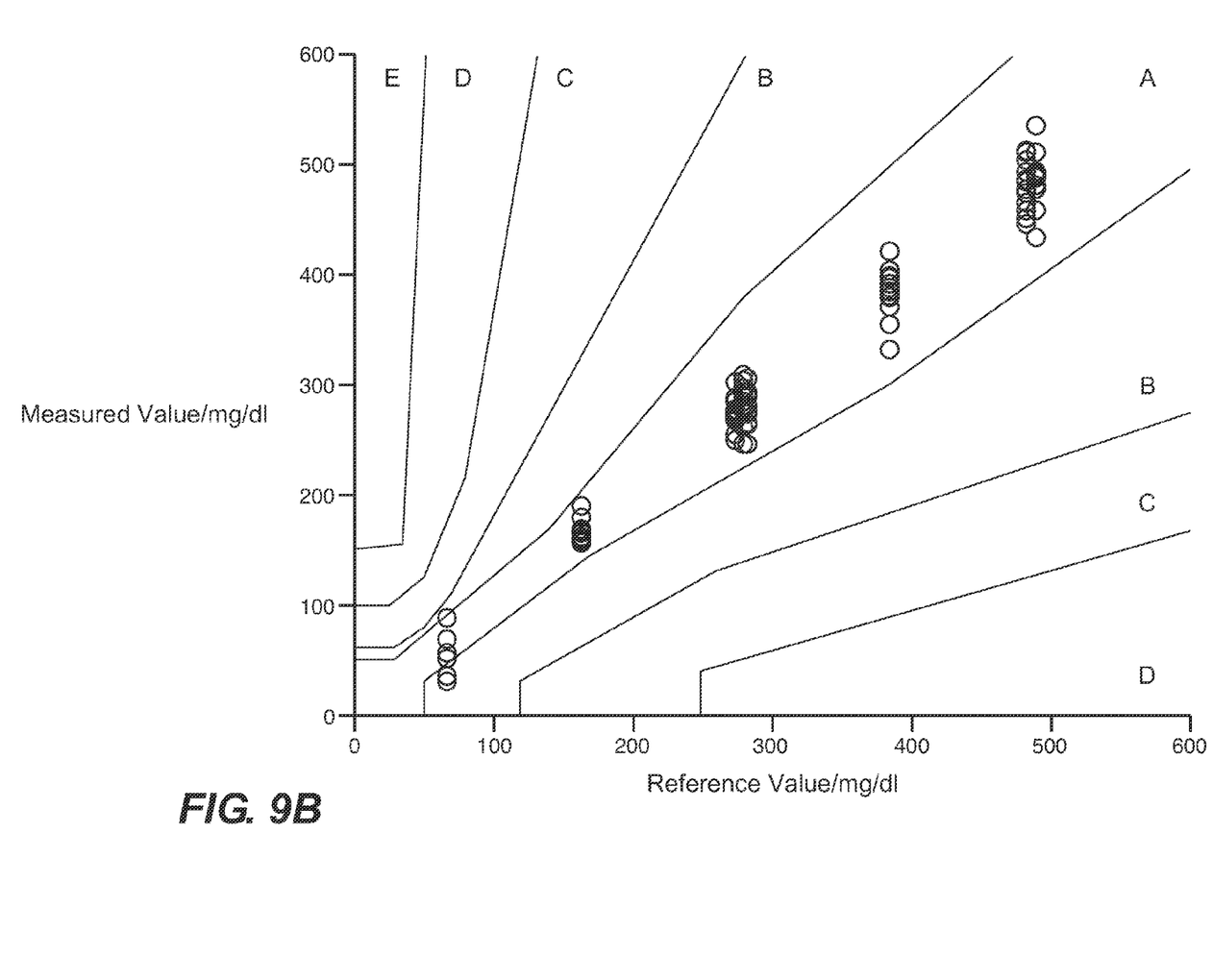
FIG. 9B illustrates a Concensus Error Grid after applying an exemplary embodiment of the subject method to the data obtained with test strips as shown in FIGS. 2 and 3.

FIGS. 9A and 9B illustrate Concensus Error Grids of test glucose concentration as a function of reference glucose concentration as determined on a reference instrument. Concensus Error Grid analysis provides a method to assess the clinical accuracy of a blood glucose monitoring device. The error grid of such an analysis categorizes a device's response against a reference value into one of five clinical accuracy zones, i.e., zones A-E. Zone A indicates clinically accurate results; zone B indicates results that are not clinically accurate but pose minimal risk to patient health; and zones C through E indicate clinically inaccurate results that pose increasing potential risk to patient health (see Parkes, Joan L. et al., *A New Consensus Error Grid to Evaluate the Clinical Significance of Inaccuracies in the Measurement of Blood Glucose*, Diabetes Care, Vol. 23 No. 8, 1143-1147 [2000]). Specifications can be developed based on the percent of results falling within the various error grid zones. In the current example, it is desirable that at least 95% of the data lie within zones A and B. FIG. 9A illustrates data that includes test results from strips that were completely filled with sample and strips that were partially filled with sample. FIG. 9B illustrates the data with results from partially filled strips removed. A summary of the percent of data falling within each zone is given in Table 1 below for all data and with data from partially filled strips removed.

TABLE 1

Summary of Consensus Error Grid Analysis

| Zone | Percent within Zone for All Data | Percent within Zone with Data Removed from Partially Filled strips |
|------|----------------------------------|--------------------------------------------------------------------|
| A    | 81.8                             | 97.6                                                               |
| B    | 3.2                              | 2.4                                                                |
| C    | 5.8                              | 0.0                                                                |
| D    | 9.0                              | 0.0                                                                |
| E    | 0.0                              | 0.0                                                                |

The data in Table 1 illustrates an increase in the percent of data points in Zone A when the data from partially filled strips are removed.

In conclusion, the system and methods described and illustrated herein can be used to determine volume sufficiency without a fill detect electrode.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining the volume sufficiency of a fluid sample applied to a test strip electrically connected to a meter for measuring a glucose concentration, the method comprising:
   providing the test strip having;
      a first working electrode;
      a shared reference electrode;
      a second working electrode;
      at least one mediator layer disposed over at least a portion of the first working electrode, at least a portion of the shared reference electrode and at least a portion of the second working electrode;
      a first analyte reagent layer disposed over at least a portion of the mediator layer disposed over at least a portion of the first working electrode; and
      a second analyte reagent layer disposed at least over a portion of the mediator layer disposed over at least a portion of the second working electrode and at least a portion of the shared reference electrode;
   depositing a physiological sample over at least a portion of one of the first and second analyte reagent layer;
   after the depositing, applying approximately a first voltage for a first time period between the first working electrode, the shared reference electrode and the second working electrode;
   measuring a first current during the first time period at the first working electrode;
   applying a voltage other than first voltage for a second time period after the first time period between the shared reference electrode and the second working electrode;
   measuring a second current at the second working electrode and the reference electrode;
   predicting an estimated second current during the second time period at the second working electrode, in which the estimated second current during the second time period is determined from the measured first current as correlated to known first current data and known second current data from sufficiently filled samples;
   evaluating a difference between the measured second current and the estimated second current during the second time period; and
   displaying an error condition indicating volume insufficiency if the difference between the measured second current during the second time period and the estimated second current during the second time period are greater than an acceptance limit.

2. The method of claim 1, in which the first voltage comprises zero volts.

3. The method of claim 1, in which the first voltage is applied between the reference electrode, the first working electrode and the second working electrode for about zero seconds to about 4 seconds.

4. The method of claim 1, in which the voltage other than first voltage for a second time period after the first time period comprises a voltage of any value from about 200 millivolts to about 500 millivolts.

5. The method of claim 1, in which the acceptance limit comprises from about −40% to about +40% between the measured and estimated second currents.

* * * * *